United States Patent [19]

Wang et al.

[11] Patent Number: 4,929,654
[45] Date of Patent: May 29, 1990

[54] CYCLIC PHOSPHITES AND STABILIZED POLYMERIC COMPOSITIONS

[75] Inventors: Richard H. S. Wang; Garry L. Myers, both of Kingsport, Tenn.

[73] Assignee: Eastman Kodak Company, Rochester, N.Y.

[21] Appl. No.: 253,168

[22] Filed: Oct. 4, 1988

[51] Int. Cl.$^5$ .................... C08K 5/524; C07D 9/15
[52] U.S. Cl. ...................... 524/117; 524/118; 524/119; 558/78; 558/85
[58] Field of Search .............. 524/117, 118, 119; 558/78, 85

[56] References Cited

U.S. PATENT DOCUMENTS

| | | | |
|---|---|---|---|
| 3,297,631 | 1/1967 | Bown et al. | 524/117 |
| 3,398,115 | 8/1968 | Hecker et al. | 524/117 |
| 4,233,208 | 11/1980 | Spivack | 524/151 |
| 4,252,750 | 2/1981 | Buysch et al. | 524/117 |
| 4,670,492 | 6/1987 | Nakahara et al. | 524/119 |
| 4,673,701 | 6/1987 | Minagawa et al. | 524/99 |

*Primary Examiner*—Kriellion Morgan
*Attorney, Agent, or Firm*—J. Frederick Thomsen; William P. Heath, Jr.

[57] ABSTRACT

Disclosed are novel cyclic phosphite compounds having the formula

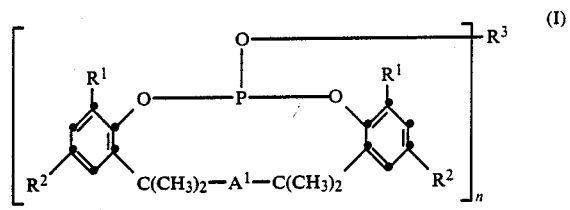

wherein
each $R^1$ is independently selected from hydrogen, alkyl, aralkyl, aryl, carboxy, alkoxycarbonyl or halogen;
each $R^2$ is independently selected from hydrogen, alkyl, aralkyl, alkoxy, aryl, carboxy, alkoxycarbonyl or halogen;
$R^3$ is (a) hydrogen, alkyl, cyclohexyl or aryl when n is 1; (b) alkylene, cyclohexylene, cyclohexylenedialkylene, arylene or a divalent group having the formula

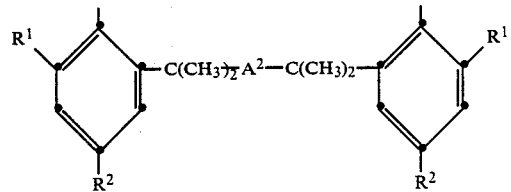

wherein $R^1$ and $R^2$ are defined above and $A^2$ is 1,3- or 1,4-phenylene when n is 2; (c) alkanetriyl when n is 3; or alkanetetrayl when n is 4;
n is 1, 2, 3 or 4; and
$A^1$ is 1,3-phenylene.

Also disclosed are synthetic polymeric materials stabilized with one of the above compounds and phosphite chloride compounds from which the above compounds are prepared.

22 Claims, No Drawings

CYCLIC PHOSPHITES AND STABILIZED POLYMERIC COMPOSITIONS

DESCRIPTION

This invention concerns certain novel cyclic phosphite compounds and polymeric materials stablized with certain of the phosphite compounds. More specifically, this invention concerns certain phosphite chlorides, hydrolytically-stable, cyclic phosphites prepared therefrom and polymeric materials stabilized against thermally-induced oxidative degradation by the presence therein of at least one of the cyclic phosphites.

Synthetic polymeric materials such as polyamides and polyolefins, particularly polypropylene, require stabilization against thermal degradation to prevent significant changes in the properties of the polymeric material during melt processing. For example, without adequate stabilization, the melt-flow rate of polypropylene changes significantly during its extrusion in the compounding of various formulations and products. Various cyclic phosphites and the use thereof in polyolefins are well-known. See, for example, U.S. Pat. Nos. 4,252,750 and 4,673,701. Many of these known cyclic phosphite compounds possess moderate to poor hydrolytic stability which causes their effectiveness as polyolefin stablilizers to diminish when they are stored over a period of time, especially in areas of high humidity. The novel cyclic phosphates provided by our invention exhibit excellent hydrolytic stability and are effective process stabilizers for polyolefins.

The cyclic phosphites of this invnetion have the general formula

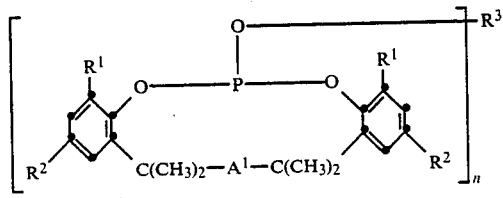

wherein
each $R^1$ is independently selected from hydrogen, alkyl, aralkyl, aryl, carboxy, alkoxycarbonyl or halogen;
each $R^2$ is independently selected from hydrogen, alkyl, aralkyl, alkoxy, aryl, carboxy, alkoxycarbonyl or halogen;
$R^3$ is (a) hydrogen, alkyl, cyclohexyl or aryl when n is 1; (b) alkylene, cyclohexylene, cyclohexylenedialkylene, arylene or a divalent group having the formula

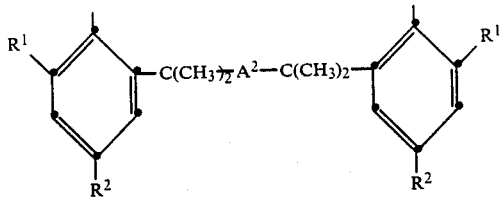

wherein
$R^1$ and $R^2$ are defined above and
$A^2$ is 1,3- or 1,4-phenylene when n is 2; (c) alkanetriyl when n is 3; or (d) alkanetetrayl when n is 4;
n is 1, 2, 3 or 4; and
$A^1$ is 1,3-phenylene.

Examples of the alkyl groups represented by $R^1$, $R^2$, and $R^3$ include alkyl containing up to about 18 carbon such as methyl, ethyl, propyl, 2-propyl, butyl, 2-butyl, 2-methyl-2-propyl, pentyl, 2-pentyl, hexyl, 2-ethylhexyl, 2,4,4-trimethyl-2-pentyl, decyl, dodecyl, hexadecyl and octadecyl. The alkyl groups represented by $R^1$ and $R^2$ preferably contain up to 8 carbon atoms. The alkoxy groups which $R^2$ can represent and the alkoxy moiety of the alkoxycarbonyl moiety of the alkoxycarbonyl groups which $R^1$ and $R^2$ can represent may contain up to about 8 carbon atoms and include methoxy, ethoxy, propxy, butoxy, hexyloxy, octyloxy and isomers thereof. The aryl groups represented by $R^1$, $R^2$ and $R^3$ and the aryl moieties of the aralkyl radicals represented by $R^1$ and $R^2$ and the arylene radicals represented by $R^3$ may be unsubstituted phenyl or phenyl substituted with 1 or 2 groups selected from lower, i.e., containing up to about 4 carbon atoms, alkyl, lower alkoxy or halogen, e.g., chlorine or bromine. The alkyl moiety of the aralkyl groups typically is lower alkyl. The alkylene radicals which $R^3$ can represent may contain up to about 8 carbon atoms. The alkanetriyl and alkanetetrayl residues which $R^3$ may represent may contain from about 3 to 8 carbon atoms.

The compounds of formula (I) may be prepared by reacting the novel phosphite chlorides of our invention having the formula

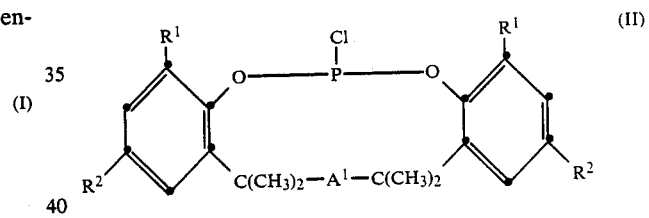

with a hydroxy compound such as water, an alkanol or phenol having the formula HO—$R^3$, a diol having the formula HO—$R^3$—OH or a triol or tetraol having the formula

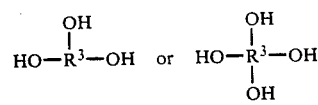

wherein $R^1$, $R^2$, $R^3$ and $A^1$ are defined above.

Examples of the hydroxy compounds include methanol, ethanol, propanol, butanol, 2-ethyl-2-propanol, 2-ethylhexanol, dodecanol, cyclohexanol, phenol, 4-methoxyphenol, 2,4-bis(2-ethyl-2-propyl)phenol, 1,2-ethanediol, 1,4-butanediol, 1,6-hexanediol, 1,4-cyclohexanedimethanol, hydroquinone, resorcinol, glycerin, trimethylolethane, trimethylolpropane and pentaerythritol. The hydroxy compound also may be one of the 1,4-bis(hydroxyphenylpropyl)benzene compounds having formula (III) described below or the 1,4-phenylene isomers thereof, preferably those wherein $R^1$ is hydrogen or alkyl of 1 to 8 carbon atoms.

The phosphite chloride compounds of formula (II) may be obtained by reacting a bis(hydroxyphenylpropyl)benzene compound having the formula

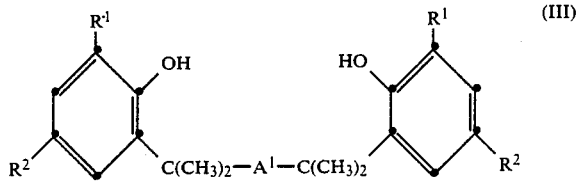

(III)

with phosphorus trichloride according to known procedures for synthesizing phosphite esters. For example, phosphorus trichloride may be added slowly or in portions to the bis(hydroxyphenylpropyl)benzene compound dissolved in an inert solvent such as a hydrocarbon. The resulting mixture then may be heated, for example in the range of 40° to 90° C., until the evolution of hydrogen chloride ceases. The hydrocarbon solution of the phosphite chloride compound may be used to prepare the compounds of formula (I). Normally, an acid acceptor, preferably one which is soluble in or miscible with the hydrocarbon solvent, is added to the solution of the phosphite chloride followed by the addition of the hydroxy compound.

The bis(hydroxyphenylpropyl)benzene compounds are prepared by reacting m- or p-diisopropenylbenzene with phenols having the formula

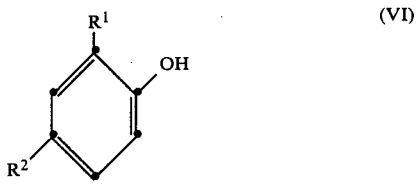

(VI)

wherein $R^1$ and $R^2$ are defined above. Example of phenols (IV) include 2-methylphenol, 2,4-bis(2-methyl-2-butyl)phenol, 4-(2,4,4-trimethyl-2-pentyl)phenol, 2,4-bis(2-methyl-2-propyl)phenol, 4-methylphenol, 2-(2-methyl-2-propyl)-4-methylphenol, 4-octylphenol, 4-dodecylphenol, 2-(2-butyl)-4-(2-methyl-2-propyl)phenol, 4-methoxyphenol, 4-chlorophenol, 4-methoxycarbonylphenol, 4-(2-phenyl-2-propyl)phenol and 2-methyl-4-(1-phenylethyl)phenol. Additional examples of phenols (IV) are given in U.S. Pat. Nos. 4,141,903, 4,219,480 and 4,275,004. Phenols (IV) also may be used as the hydroxy compound reacted with phosphite chlorides (II).

The compounds of our invention which are preferred are those of formula (I) wherein $R^1$ is hydrogen or alkyl of up to about 8 carbon atoms;

$R^2$ is alkyl or alkoxy of up to about 8 carbon atoms, phenylalkyl of 7 to about 9 carbon atoms, chloro or methoxycarbonyl;

n is 1 or 2; and $R^3$ is hydrogen, alkyl of up to about 18 carbon atoms, alkylene of 2 to about 10 carbon atoms or phenylene.

The cyclic phosphite compounds of our invention and their preparation are further illustrated by the following examples.

EXAMPLE 1

Phosphorus trichloride (0.32 mol) is added dropwise over a 20 minute period with a stream of nitrogen to a solution of 1,3-bis[2-[2-(2-hydroxy-5-methylphenyl)]-propyl]benzene(0.267 mol) in 1 liter of toluene at 70° C. The evolution of hydrogen chloride ceases after heating at 70° C. for 6.5 hours. The toluene solution then is cooled to 5° C. and water (0.426 mol) is added dropwise. The mixture is stirred at 5° C. for 1 hours while sparging with nitrogen. The solvent is stripped off to give 110 g (97% of theory) of product having the structure:

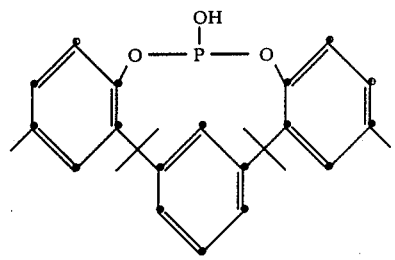

FDMS MW=420; M.P.=78°-83° C.

EXAMPLE 2

Pyridine (300 mL) and methanol (1.25 mol) are added successively to a 5° C. toluene solution of phosphite chloride intermediate prepared as described in Example 1. The resulting mixture is stirred at 5° C. for 1 hour and then filtered to remove pyridinium salt. The crude product, obtained upon the removal of the solvent, is recrystallized from heptanemethanol to give an 81% yield product having the structure:

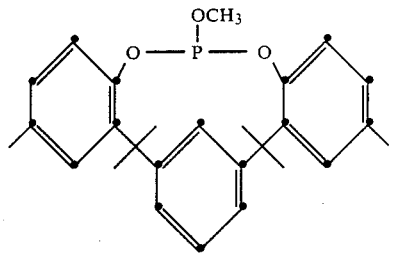

FDMS MW=434; M.P.=84°-85° C.

EXAMPLE 3

Pyridine (20 mL) and 2,4-bis-(2-methyl-2-propyl)-phenol (0.02 mol) are added succesively to a toluene solution of 0.02 mol of the phosphite chloride prepared according to Example 1. The mixture is stirred at 70° C. for 15 minutes and then allowed to stand overnight. The mixture is filtered followed by removal of the solvent to give a 77% yield of product having the structure

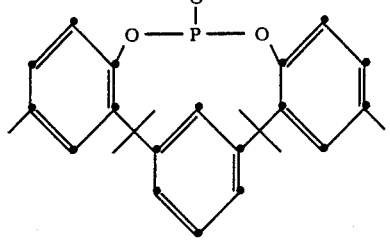

Elemental analysis, Calc. for C40H49O3P: C,78.90; P, 5.10 ; Found: C, 78.00; P, 5.05 ; FDMS MW=608.

EXAMPLE 4

Example 2 is repeated using octanol rather than methanol to obtain a 59% yield of the cyclic phosphite having the structure

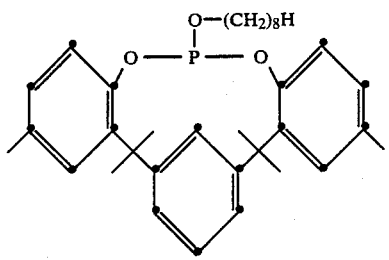

FSMS MW=532.

EXAMPLE 5

Example 2 is repeated using neopentyl glycol rather than methanol to obtain a 73% yield of the bis-cyclic phosphite having the structure

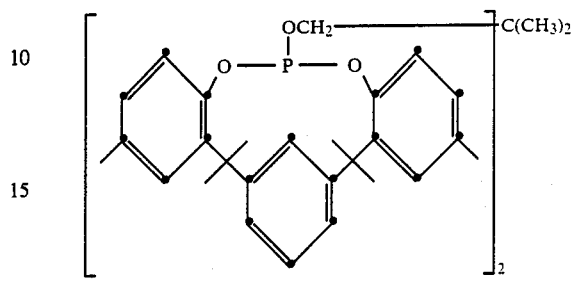

Elemental analysis, Calc. for C57H66O6P2: C, 75.33; H, 7.30 ; Found: C, 75.35; H, 7.88; FDMS MW=908.

EXAMPLE 6

Example 2 is repeated using 1.4-cyclohexanedimethanol rather than methanol to obtain a 69% yield of the bis-cyclic phosphite having the structure

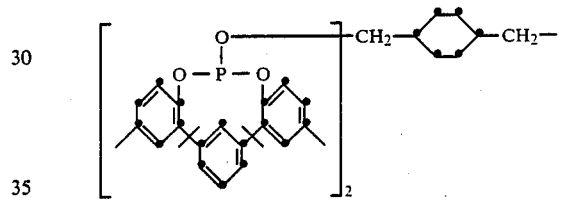

FSMS MW=948.

TABLE

| Example | R$^1$ | R$^2$ | R$^3$ | n |
|---|---|---|---|---|
| 7 | H | —C(CH$_3$)$_3$ | —CH$_3$ | 1 |
| 8 | —CH$_3$ | —C(CH$_3$)$_3$ | —CH$_3$ | 1 |
| 9 | —C(CH$_3$)$_3$ | —C(CH$_3$)$_3$ | —CH$_3$ | 1 |
| 10 | H | —CH$_3$ | —C$_6$H$_4$— | 2 |
| 11 | H | —CH$_3$ | —C$_6$H$_2$-2,5-di-C(CH$_3$)$_3$— | 2 |
| 12 | H | —CH$_3$ | (terphenyl with two CH$_3$ groups) | 2 |
| 13 | H | —CH$_3$ | (terphenyl with two CH$_3$ groups) | 2 |
| 14 | H | —C(CH$_3$)$_2$—CH$_2$—C(CH$_2$)$_3$ | —CH$_3$ | 1 |
| 15 | H | —Cl | —CH$_3$ | 1 |

TABLE-continued

| Example | R¹ | R² | R³ | n |
|---|---|---|---|---|
| 16 | H | —COCH₃ (C=O) | —CH₃ | 1 |
| 17 | —CH₃ | —CH₃ | —CH₃ | 1 |
| 18 | H | —(CH₃)₂—(phenyl) | —CH₃ | 1 |
| 19 | H | —CH₃ | CH₂—<br>\|<br>CH—<br>\|<br>CH₂— | 3 |
| 20 | H | —CH₃ | C(CH₂—)₄ | 4 |

Additional cyclic phosphite compounds provided by our invention are set forth in the Table I. These compounds, which conform to formula (I), may be prepared by the procedures described hereinabove by reacting the appropriate bis-(hydroxyphenylpropyl)benzene compound (III) with phosphorus trichloride and reacting the intermediate phosphite chloride with an hydroxy compound.

The hydrolytic stability of the cyclic phosphite compounds described above and two known phosphite compounds are evaluated by placing a weighed sample (10 g) of each phosphite compound in an oven at 60° C. and 100% humidity. At intervals of 2, 6, 10 and 31 hours, the samples are removed from the oven and weighed to determine the amount (weight percent) of water which has been absorbed by each sample. The total water absorbed by each sample each time the samples are weighed is shown in Table II. Phosphite compounds A, B and C are the cyclic phosphite compounds prepared in Examples 1, 2 and 3, respectively. Phosphites D and E have the structures:

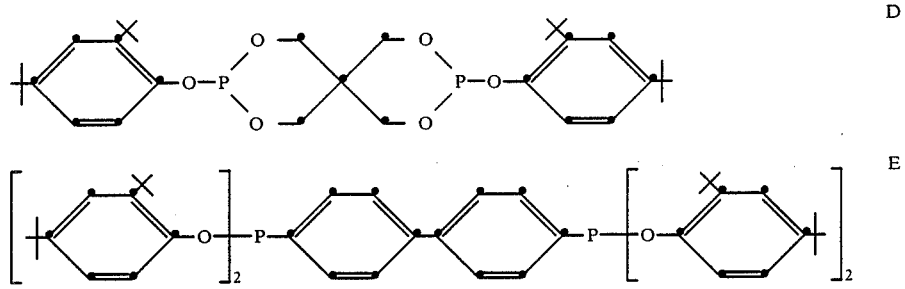

TABLE II

| Interval, | Water Absorbed Phosphite Compound | | | | |
|---|---|---|---|---|---|
| hours | A | B | C | D | E |
| 2 | 0.5 | 0 | 0 | 1.3 | 0 |
| 6 | 0.5 | 0 | 0 | 6.7 | 0.9 |
| 10 | 0.5 | 0 | 0 | 8.3 | 0.9 |
| 31 | 1.5 | 1.3 | 0 | 10.2 | 2.0 |

Each sample of the phosphite compounds C, D and E are analyzed initially and at intervals of 2.5, 4.5 and 25.5 hours by gas chromatography for the presence of 2,4-bis-(2-methyl-2-propyl)phenol, a product of hydrolytic degradation. The mole percent of the phenol detected is shown in Table III.

TABLE III

| Interval, | Mole Percent Phenol Phosphite Compound | | |
|---|---|---|---|
| hours | C | D | E |
| 0 | 0 | 1.3 | 5.9 |
| 2.5 | 1.9 | 2.5 | 8.2 |
| 4.5 | 2.4 | — | 10.6 |
| 25.5 | 3.9 | 70.0 | 27.3 |

The cyclic phosphite compounds of formula (I) may be used in a wide variety of synthetic polymeric materials which are susceptible to degradation upon exposure to heat and/or radiation including both visible and ultraviolet light. Examples of such polymeric materials include homo- and co-polymers of α-olefins such as polyethylene, polypropylene, polybutene, poly-3-methylbutene and ethylenepropylene copolymers, ehtylene-vinyl acetate copolymers, polystyrene, copolymers of styrene with other ethylenically-unsaturated monomers such as maleic anhydride, butadiene and acrylonitrile, polyvinyl acetate, acrylonitrile-butadiene-styrene polymers, polymethacrylate polymers, polyvinyl formal, polyvinyl butryal, polyamides such as polycaprolactum (nylon 6), polycarbonates, unsaturated polyesters and polyvinylidene chloride. The preferred stabilized compositions of our invention comprise homo- and co-polymers of α-olefins of 2 to 4 carbon atoms, especially polypropylene, containing a stabilizing amount of one or more of the compounds of formula (I).

The concentration of the phosphite compound in the polymeric material which will effectively inhibit polymer degradation can vary considerably depending on the particular polymer being stabilized and the end use for which the stabilized polymeric material is designed. Generally, concentration in the range of 0.001 to 5.0 weight percent may be used with concentrations of about 0.01 to 0.5 being most common. The phosphite stabilizers provided by this invention typically will be used in combination with other conventional stabilizers such as phenolic antioxidants, polyvalent salts of organic acids and thioethers. In addition, other additives such as plasticizers, lubricants, emulsifiers, antistatic agents, flame retardant agents, pigments and fillers, commonly used in formulating commercial polymeric compositions may be present.

The phosphite stabilizer may be incorporated into the polymeric materials by conventional blending techniques. For example, the stabilizer may be added directly to a melt of the polymer on a roll mill to distribute the phosphite compound uniformly throughout the polymer. Alternatively, the phosphite compound may be dry-blended with a finely-divided form of the polymer such as pellets and then the dry mix can be mixed further in and extruded from an extruder.

Samples of polypropylene containing 0.05 phr (parts by weight per 100 parts by weight polypropylene) calcium stearate, 0.03 phr glycerol and 0.05 phr 2,2-bis[[3-3,5-bis-(1,1-dimethylethyl)-4-hydroxyphenyl-]-1-oxo-pro-poxy]-methyl]-1,3-propanediyl 3,5-bis(1,1-dimethylethyl)-4-hydroxybenzenepropanoate (Irganox 1010 stablizer), without any phosphite compound and with 0.03 phr of phosphite compound A, B or D are prepared by shaking the additives and polypropylene pellets together in a plastic bag and then blending the dry mix in and extruding each sample from a Brabender single screw rod extruder at 230° C. Each polypropylene sample was extruded five times. After each extrusion, the melt-flow rate (ASTM Method D 1238, Procedure A, Condition E; g/10 minutes, MFR) and yellowness index (ASTM Method D 1925; b value) are measured for each sample. The inhibiting effect of each phosphite compound on the thermal degradation of the polypropylene is shown in Table IV.

TABLE IV

| Phosphite Compound | 1st Extrusion | | 3rd Extrusion | | 5th Extrusion | |
|---|---|---|---|---|---|---|
| | b value | MFR | b value | MFR | b value | MFR |
| None | 9.1 | 4.2 | 9.3 | 5.0 | 11.6 | 6.3 |
| A | 10.2 | 0.8 | 12.6 | 1.4 | 12.7 | 1.9 |
| B | 9.1 | 1.0 | 11.4 | 1.2 | 13.8 | 1.6 |
| D | 8.0 | 1.1 | 9.1 | 1.3 | 11.1 | 2.0 |

The invention has been described in detail with particular reference to preferred embodiments thereof, but it will be understood that variations and modifications will be effected within the spirit and scope of the invention.

We claim:

1. A compound having the formula

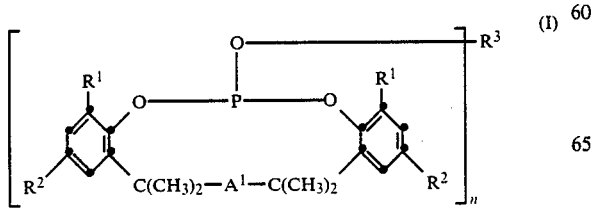

(I)

wherein
each $R^1$ is independently selected from hydrogen, alkyl, aralkyl, aryl, carboxy, alkoxycarbonyl or halogen;
each $R^2$ is independently selected from hydrogen, alkyl, aralkyl, alkoxy, aryl, carboxy, alkoxycarbonyl or halogen;
$R^3$ is (a) hydrogen, alkyl, cyclohexyl or aryl when n is 1; (b) alkylene, cyclohexylene, cyclohexylenedialkylene, arylene or a divalent group having the formula

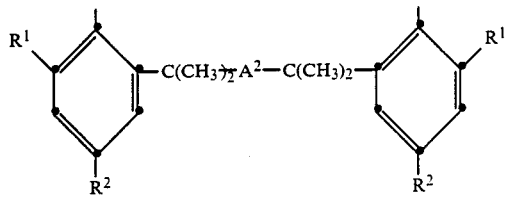

wherein
$R^1$ and $R^2$ are defined above and
$A^2$ is 1,3- or 1,4-phenylene when n is 2; (c) alkanetriyl when n is 3; or (d) alkanetetrayl when n is 4;
n is 1, 2, 3 or 4; and
$A^1$ is 1,3-phenylene.

2. A compound according to claim 1 having the formula

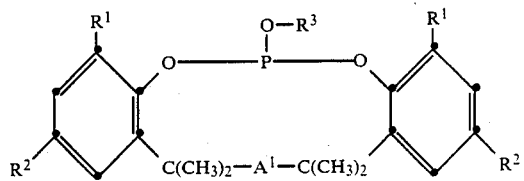

wherein $R^3$ is hydrogen, alkyl or aryl.

3. A compound according to claim 2 wherein
$R^1$ is hydrogen or alkyl of up to about 8 carbon atoms;
$R^2$ is alkyl or alkoxy of up to about 8 carbon atoms, phenylalkyl of 7 to about 9 carbon atoms, chloro or methyoxycarbonyl; and
$R^3$ is hydrogen or alkyl of up to about 18 carbon atoms.

4. A compound according to claim 1 having the formula

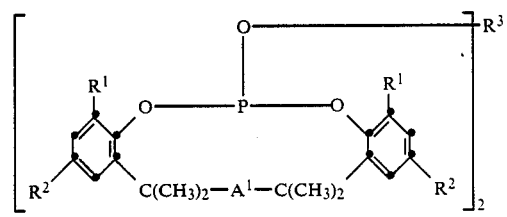

wherein $R^3$ is alkylene, cyclohexylene, cyclohexylenedialkylenee or arylene.

5. A compound according to claim 4 wherein
$R^1$ is hydrogen or alkyl of up to about 8 carbon atoms;
$R^2$ is alkyl or alkoxy of up to about 8 carbon atoms, phenylalkyl of 7 to about 9 carbon atoms, chloro or methoxycarbonyl; and R³ is alkylene of 2 to about 10 carbon atoms or phenylene.

6. A compound according to claim 1 having the formula

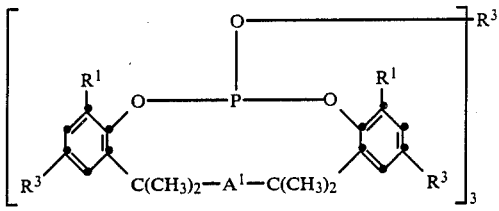

wherein R³ is alkanetriyl.

7. A compound according to claim 6 wherein
R¹ is hydrogen or alkyl of up to about 8 carbon atoms;
R² is alkyl or alkoxy of up to about 8 carbon atoms, phenylalkyl of 7 to about 9 carbon atoms, chloro or methoxycarbonyl; and
R³ is alkanetriyl of about 3 to 8 caron atoms.

8. A compound according to claim 1 having the formula

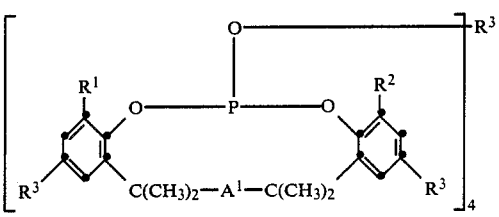

wherein R³ is alkanetetrayl.

9. A compound according to claim 6 wherein
R¹ is hydrogen or alkyl of up to about 8 carbon atoms;
R² is alkyl or alkoxy of up to about 8 carbon atoms, phenylalkyl of 7 to about 9 carbon atoms, chloro or methoxycarbonyl; and
R³ is alkenetetrayl of about 3 to 8 caron atoms.

10. A compound having the formula

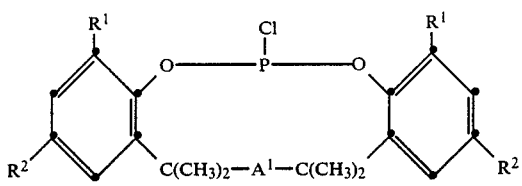

wherein
each R¹ is independently selected from hydrogen, alkyl, aralkyl, aryl, carboxy, alkoxycarbonyl or halogen;
each R² is independently selected from hyrogen, alkyl, aralkyl, alkoxy, aryl, carboxy, alkoxycarbonyl or halogen; and
A¹ is 1,3-phenylene.

11. A compound according to claim 10 wherein
R¹ is hydrogen or alkyl of up to about 8 carbon atoms; and
R² is alkyl or alkoxy of up to about 8 carbon atoms, phenylalkyl of 7 to about 9 carbon atoms, chloro or methoxycarbonyl.

12. A stabilized composition comprising a synthetic polymeric material susceptible to degradation upon exposure to heat and/or radiation containing a stabilizing amount of a compound defined in claim 1.

13. A stabilized composition comprising a synthetic polymeric material susceptible to degradation upon exposure to heat and/or radiation containing a stabilizing amount of a compound defined in claim 2.

14. A stabilized composition comprising a synthetic polymeric material susceptible to degradation upon exposure to heat and/or radiation containing about 0.01 to 0.5 weight percent based on the weight of the polymeric material of a compound defined in claim 1.

15. A stabilized composition comprising a synthetic polymeric material susceptible to degradation upon exposure to heat and/or radiation containing about 0.01 to 0.5 weight percent based on the weight of the polymeric material of a compound defined in claim 2.

16. A stablized composition comprising a synthetic polymeric material susceptible to degradation upon exposure to heat and/or radiation containing about 0.01 to 0.5 weight percent based on the weight of the polymeric material of a compound defined in claim 4.

17. A stabilized composition comprising a synthetic polymeric material sysceptible to degradation upon exposure to heat and/or radiation containing from 0.01 to 0.5 weight percent based on the weight of the polymeric material of compound defined in claim 6.

18. A stabilized composition comprising a synthetic polymeric material susceptible to degradation upon exposure to heat and/or radiation containing from 0.01 to 0.5 weight percnet based on the weight of the polymeric material of a compound defined in claim 8.

19. A stabilized composition comprising an α-olefin homo- or co-polymer containing a stabilizing amount of a compound defined in claim 1.

20. A stabilized composition comprising polypropylene containing a stabilizing amount of a compound defined in claim 1.

21. A stabilized composition comprising an α-olefin homo- or co-polymer containing from about 0.01 to 0.05 weight percent based on the weight of the α-olefin polymer of a compound defined in claim 2.

22. A stabilized composition comprising an α-olefin homo- or co-polymer containing from about 0.01 to 0.05 weight percent based on the weight of the α-olefin polymer of a compound defined in claim 4.

* * * * *

UNITED STATES PATENT AND TRADEMARK OFFICE
CERTIFICATE OF CORRECTION

PATENT NO. : 4,929,654

DATED : May 29, 1990

INVENTOR(S) : Richard H.S. Wang and Garry L. Myers

It is certified that error appears in the above-identified patent and that said Letters Patent is hereby corrected as shown below:

Column 10, line 46, "methyoxycarbonyl" should be ---methoxycarbonyl---.

Column 11, line 21, "phenyalkyl" should be ---phenylalkyl---.

Column 11, line 23, "caron." should be ---carbon---.

Column 11, line 43, "alkenetetrayl" should be ---alkanetetrayl---.

Column 11, line 43, "caron" should be ---carbon---.

Column 12, line 38, before "compound" insert ---a---.

Column 12, line 42, "percnet" should be ---percent---.

Signed and Sealed this

Fifteenth Day of October, 1991

Attest:

*Attesting Officer*

HARRY F. MANBECK, JR.

*Commissioner of Patents and Trademarks*